United States Patent
Sterk et al.

(12)

(10) Patent No.: US 6,255,303 B1
(45) Date of Patent: Jul. 3, 2001

(54) PHTHALAZINONE PDE III/IV INHIBITORS

(75) Inventors: Geert Jan Sterk, Utrecht; Margaretha van der Mey, Rijnsburg, both of (NL)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/623,477

(22) PCT Filed: Mar. 4, 1999

(86) PCT No.: PCT/EP99/01413

§ 371 Date: Sep. 13, 2000

§ 102(e) Date: Sep. 13, 2000

(87) PCT Pub. No.: WO99/47505

PCT Pub. Date: Sep. 23, 1999

(30) Foreign Application Priority Data

Mar. 14, 1998 (AT) .................................. 98104643

(51) Int. Cl.$^7$ ..................... A61K 31/54; A61K 31/502; C07D 403/10; C07D 417/10

(52) U.S. Cl. ..................... 514/222.5; 514/248; 544/8; 544/237

(58) Field of Search ................ 544/237, 8; 514/248, 514/222.5

(56) References Cited

U.S. PATENT DOCUMENTS 6,103,718 * 8/2000 Sterk .................. 514/234.3

FOREIGN PATENT DOCUMENTS

634404 * 1/1995 (EP) .
763534 * 3/1997 (EP) .
2112389 * 7/1983 (GB) .
94/12461 * 6/1994 (WO) .

OTHER PUBLICATIONS

Maki et al, *Rapid Communications in Mass Spectrometry*, vol. 8, p 1021–1025, 1994.*
Stajer et al, *Monatshefte für Chemie*, 125, p 933–934, 1994.*

* cited by examiner

*Primary Examiner*—Emily Bernhardt
(74) *Attorney, Agent, or Firm*—Jacobson Holman PLLC

(57) ABSTRACT

The compounds of formula (I) in which R1, R2, R3, R4, R5, X and Y have the meanings as given in the description are novel effective bronchial therapeutica.

8 Claims, No Drawings

PHTHALAZINONE PDE III/IV INHIBITORS

FIELD OF APPLICATION OF THE INVENTION

The invention relates to novel Phthalazinones, which are used in the pharmaceutical industry for the production of medicaments.

KNOWN TECHNICAL BACKGROUND

International Patent Application WO91/12251 describes phthalazinones having bronchodilating and thromboxane A2 synthetase inhibiting properties. In the International Patent Application WO94/12461 and in the European Patent Application EP 0 763 534 3-aryl-pyridazin-6-one respectively arylalkyl-diazinone derivatives are described as selective PDE4 inhibitors.

DESCRIPTION OF THE INVENTION

It has now been found that the phthalazinones, which are described in greater details below, have surprising and particularly advantageous properties.

The invention thus relates to compounds of the formula I

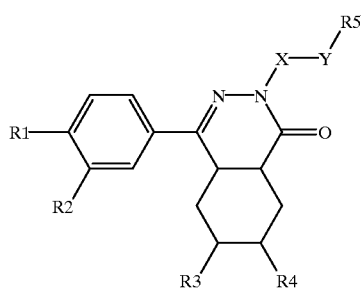

(I)

in which

R1 is hydroxyl, 1–4C-alkoxy, or 1–4C-alkoxy which is completely or predominantly substituted by fluorine, R2 is hydroxyl, halogen, 1–8C-alkoxy, 3–7C-cycloalkoxy, 3–7C-cycloalkylmethoxy, or 1–4C-alkoxy which is completely or predominantly substituted by fluorine, R3 and R4 are both hydrogen or together form an additional bond, and in which either X is a covalent bond and Y is a covalent bond, or X is —$C_nH_{2n}$— and Y is O (oxygen), S (sulfur), carboxylate (—C(O)—O—), carboxamido (—C(O)NH—) or sulfonamido (—S(O)$_2$—NH—), or X is phenylene and Y is carboxylate (—C(O)O—), carboxamido (—C(O)NH—) or sulfonamido (—S(O)$_2$NH—), R5 represents a radical of formula (a)

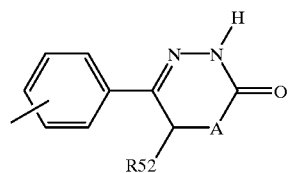

(a)

wherein

A is S (sulphur) or —CH(R51)—,

R51 is hydrogen or 1–4C-alkyl,

R52 is hydrogen or 1–4C-alkyl, or wherein

R51 and R52 together form an additional bond, n is an Integer from 1 to 4, and the salts of these compounds.

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–4C-Alkoxy is a radical, which, in addition to the oxygen atom contains a straight-chain or branched alkyl radical having 1 to 4 carbon atoms. Alkoxy radicals having 1 to 4 carbon atoms which may be mentioned in this context are, for example, the butoxy, iso-butoxy, sec-butoxy, tert-butoxy, propoxy and in particular the isopropoxy, ethoxy and methoxy radicals.

1–4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1–4C-alkoxy group are replaced by fluorine atoms.

Halogen within the meaning of the present invention is bromine, chlorine and fluorine.

1–8C-Alkoxy is a radical which, in addition to the oxygen atom, contains a straight-chain or branched alkyl radical having 1 to 8 carbon atoms. Alkoxy radicals having 1 to 8 carbon atoms which may be mentioned in this context are, for example, the octyloxy, heptyloxy, isoheptyloxy (5-methylhexyloxy), hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy and in particular the isopropoxy, ethoxy and methoxy radicals.

3–7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are preferred.

3–7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopentylmethoxy are preferred.

Possible radicals —$C_nH_{2n}$— are straight chain or branched radicals. Examples which may be mentioned are the butylene, isobutylene, sec-butylene, tert-butylene, propylene, isopropylene, ethylene and the methylene radical.

Suitable salts for compounds of the formula I—depending on substitution—are all acid addition salts or all salts with bases. Particular mention may be made of the pharmacologically tolerable inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of the formula I to be emphasized are those in which

R1 is hydroxyl, 1–4C-alkoxy, or 1–2C-alkoxy which is completely or predominantly substituted by fluorine, R2 is hydroxyl, halogen, 1–4C-alkoxy, 3–5C-cycloalkoxy, 3–5C-cycloalkylmethoxy, or 1–2C-alkoxy which is completely or predominantly substituted by fluorine, R3 and R4 are both hydrogen or together form an additional bond, and in which either X is a covalent bond and
Y is a covalent bond or X is —$C_nH_{2n}$— and
Y is O (oxygen), carboxamido (—C(O)NH—) or sulfonamido (—S(O)$_2$NH—), or X is phenylene and
Y is carboxamido (—C(O)NH—) or sulfonamido (—S(O)$_2$NH—), R5 represents a radical of the formula (a)

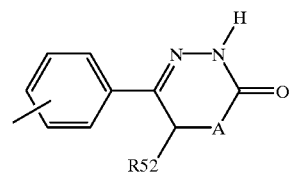

(a)

wherein
A is S (sulphur) or —CH(R51)—,
R51 is hydrogen or 1–2C-alkyl,
R52 is hydrogen or 1–2C-alkyl, or wherein
R51 and R52 together form an additional bond,
n is an integer from 1 to 4,
and the salts of these compounds.

Compounds of the formula I which are particulary to be emphasized are those in which R1 is methoxy, ethoxy or difluoromethoxy, R2 is chlorine, methoxy, ethoxy, difluoromethoxy or cyclopentyloxy, R3 and R4 are both hydrogen or together form an additional bond, and in which either X is a covalent bond and
Y is a covalent bond or X is —$C_nH_{2n}$— and
Y is O (oxygen) or carboxamido (—C(O)NH—)

or

X is phenylene and
Y is carboxamido (—C(O)NH—),

R5 represents a radical of formula (a)

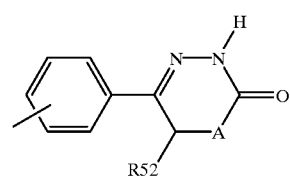

(a)

wherein
A is S (sulphur) or —CH(R51)—,
R51 is hydrogen,
R52 is methyl, or wherein
R51 and R52 together form an additional bond,
n is an integer from 1 to 4,
and the salts of these compounds.

One embodiment of the particulary to be emphasized compounds of the formula I are those in which R1 is methoxy or difluoromethoxy, R2 is methoxy, difluoromethoxy or cyclopentyloxy, R3 and R4 are both hydrogen or together form an additional bond, and in which either X is a covalent bond and
Y is a covalent bond or X is —$C_nH_{2n}$— and Y is O (oxygen) or carboxamido (—C(O)NH—)
or
  X is phenylene and
  Y is carboxamido (—C(O)NH—),
  R5 represents a radical of formula (a)

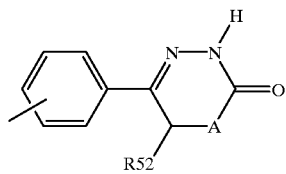

(a)

wherein
  A is S (sulphur) or —CH(R51)—,
  R51 is hydrogen,
  R52 is methyl, or wherein
  R51 and R52 together form an additional bond,
n is an integer from 1 to 4,
and the salts of these compounds.
Preferred compounds of formula I are those in which
  R1 is methoxy or ethoxy,
  R2 is chlorine, methoxy, ethoxy or cyclopentyloxy,
  R3 and R4 are both hydrogen or together form an additional bond,
and in which either
  X is a covalent bond and
  Y is a covalent bond
or
  X is —$C_nH_{2n}$— and
  Y is O (oxygen) or carboxamido (—C(O)NH—)
or
  X is phenylene and
  Y is carboxamido (—C(O)NH—),
  R5 represents a radical of formula (a)

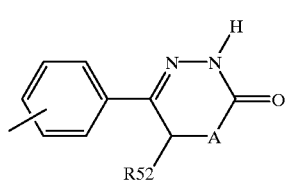

(a)

wherein
  A is S (sulphur) or —CH(R51)—,
  R51 is hydrogen,
  R52 is methyl, or wherein
  R51 and R52 together form an additional bond,
n is an integer from 1 to 4,
and the salts of these compounds.
One embodiment of the preferred compounds of the formula I are those in which
  R1 is methoxy,
  R2 is methoxy or cyclopentyloxy,
  R3 and R4 are both hydrogen or together form an additional bond,
and in which either
  X is a covalent bond and
  Y is a covalent bond or
  X is —$C_nH_{2n}$— and
  Y is O (oxygen) or carboxamido (—C(O)NH—)
or
  X is phenylene and
  Y is carboxamido (—C(O)NH—),
  R5 represents a radical of formula (a)

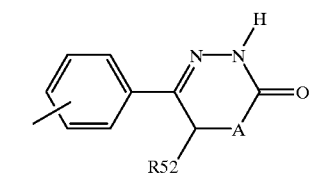

(a)

wherein
  A is S (sulphur) or —CH(R51)—,
  R51 is hydrogen,
  R52 is methyl, or wherein
  R51 and R52 together form an additional bond,
n is an integer from 1 to 4,
and the salts of these compounds.
The compounds of formula I are chiral compounds with chiral centers in the positions 4a and 8a

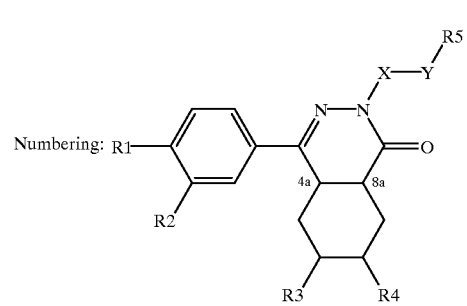

(I)

Numbering:

Therefore the invention includes all conceiveable pure diastereomers and pure enantiomers, as well as all mixtures thereof independent from the ratio, including the racemates. Preferred are those compounds, in which the hydrogen atoms in the positions 4a and 8a are cis-configurated. Especially preferred in this connection are those compounds, in which the absolute configuration (according to the rules of Cahn, Ingold and Prelog) is S in the position 4a and R in the position 8a. Racemates can be split up into the corresponding enantiomers by methods known by a person skilled in the art. Preferably the racemic mixtures are separated into two diastereomers with the help of an optical active separation agent on the stage of the cyclohexanecarboxylic acids (for example, starting compound A5) or the 1,2,3,6-tetrahydrobenzoic acids (for example, starting compound A1). As separation agents may be mentioned, for example, optical active amines such as the (+)- and (−)-forms of a-phenylethylamine and ephedrine, or the optical active alkaloids cinchonine, cinchonidine and brucine.
The invention further relates to processes for the preparation of compounds of formula I and their salts (compare Table 1).

TABLE 1

Preparation Methods

| R1 | R2 | R3 | R4 | X | Y | R5 | Method |
|---|---|---|---|---|---|---|---|
| Hydroxyl, 1-4C-alkoxy, 1-4C-fluorinated alkoxy | Hydroxyl, halogen, 1-8C-alkoxy, 1-4C-fluorinated alkoxy, 3-7C-cycloalkoxy, 3-7C-cycloalkylmethoxy | H | H | covalent bond | covalent bond | 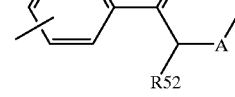 | A |
| | | together form an additional bond | | covalent bond | covalent bond | | A |
| Hydroxyl, 1-4C-alkoxy, 1-4C-fluorinated alkoxy | Hydroxyl, halogen, 1-8C-alkoxy, 1-4C-fluorinated alkoxy, 3-7C-cycloalkoxy, 3-7C-cycloalkylmethoxy | H | H | —$C_nH_{2n}$— |  | 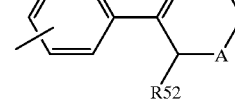 | B |
| | | together form an additional bond | | | | | B |
| Hydroxyl, 1-4C-alkoxy, 1-4C-fluorinated alkoxy | Hydroxyl, halogen, 1-8C-alkoxy, 1-4C-fluorinated alkoxy, 3-7C-cycloalkoxy, 3-7C-cycloalkylmethoxy | H | H | —$C_nH_{2n}$— |  | 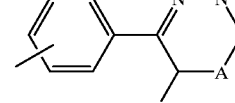 | B |
| | | together form an additional bond | | | | | B |
| Hydroxyl, 1-4C-alkoxy, 1-4C-fluorinated alkoxy | Hydroxyl, halogen, 1-8C-alkoxy, 1-4C-fluorinated alkoxy, 3-7C-cycloalkoxy, 3-7C-cycloalkylmethoxy | H | H | —$C_nH_{2n}$— |  | 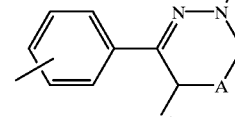 | B |
| | | together form an additional bond | | | | | B |
| Hydroxyl, 1-4C-alkoxy, 1-4C-fluorinated alkoxy | Hydroxyl, halogen, 1-8C-alkoxy, 1-4C-fluorinated alkoxy, 3-7C-cycloalkoxy, 3-7C-cycloalkylmethoxy | H | H | —$C_nH_{2n}$— | O, S | 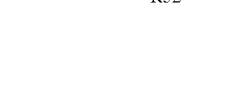 | C |
| | | together form an additional bond | | | | | C |
| Hydroxyl, 1-4C-alkoxy, 1-4C-fluorinated alkoxy | Hydroxyl, halogen, 1-8C-alkoxy, 1-4C-fluorinated alkoxy, 3-7C-cycloalkoxy, 3-7C-cycloalkylmethoxy | H | H | 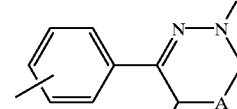 | | | B |
| | | together form an additional bond | | | | | B |

TABLE 1-continued

Preparation Methods

| R1 | R2 | R3 | R4 | X | Y | R5 | Method |
|---|---|---|---|---|---|---|---|
| Hydroxyl, 1-4C-alkoxy, 1-4C-fluorinated alkoxy | Hydroxyl, halogen, 1-8C-alkoxy, 1-4C-fluorinated alkoxy, 3-7C-cycloalkoxy, 3-7C-cycloalkylmethoxy | H | H | | | | B |
| | | together form an additional bond | | | | | B |
| Hydroxyl, 1-4C-alkoxy, 1-4C-fluorinated alkoxy | Hydroxyl, halogen, 1-8C-alkoxy, 1-4C-fluorinated alkoxy, 3-7C-cycloalkoxy, 3-7C-cycloalkylmethoxy | H | H | | | | B |
| | | together form an additional bond | | | | | B |

Method A:

Compounds of formula I in which R1, R2, R3, R4 and R5 have the above-mentioned meanings and X and Y represent a covalent bond are preferably prepared by reacting a keto acid of formula II

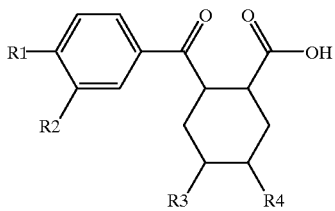
(II)

or one of its reactive derivatives, in which R1, R2, R3 and R4 have the above-mentioned meanings with a hydrazine derivative of the formula R5—NH—NH$_2$ in which R5 has the above-mentioned meanings.

The reaction of the keto acids of formula II or one of their reactive derivatives with a hydrazine derivative of formula R5—NH—NH$_2$ is advantageously carried out with one to three equivalents of the hydrazine derivatives of formula R5—NH—NH$_2$. As solvent are preferably used alcohols such as methanol, ethanol, n-propanol, isopropanol, n-butanol, isoamylalcohol, ethers, glycols and their ethers such as ethylene glycol, diethylene glycol, ethylene glycol monomethyl or ethylene glycol monoethyl ether and especially water soluble ethers such as tetrahydrofuran or dioxane; further toluene or benzene, especially when the method of azeotropic destination is used to remove the reaction water.

Keto acids of the formula II, in which R1, R2, R3 and R4 have the above-mentioned meanings can, for example, be prepared from compounds of the formula III,

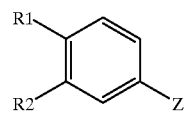
(III)

in which R1 and R2 have the above-mentioned meanings and Z represents hydrogen (H) by Friedel-Crafts acylation with compounds of the formula IV,

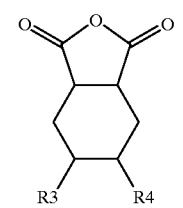
(IV)

in which R3 and R4 have the above-mentioned meanings. The Friedel-Crafts acylation is carried out in a manner which in known by the skilled person (for example as described in M. Yamaguchi et al., J. Med. Chem. 36: 4052–4060, 1993) in presence of a suitable catalyst, such as for example, AlCl$_3$, ZnCl$_2$, FeCl$_3$ or iodine, in an appropriate inert solvent, such as methylene chloride or nitrobenzene or another inert solvent such as diethylether, preferably at raised temperature, in particular at the boiling point of the solvent used.

Alternatively, the compounds of formula II, in which R1, R2, R3 and R4 have the above-mentioned meanings, can be prepared from compounds of the formula III, in which R1 and R2 have the above-mentioned meanings and Z represents a halogen atom through reaction with compounds of the formula IV, in which R3 and R4 have the above-mentioned meanings.

The alternative reaction, which is mentioned in the previous paragraph is carried out in a manner which is known by a person skilled in the art, for example a) by activating compounds of formula III, in which R1, R2 and Z have the above-mentioned meanings, by a lithium/halogen exchange reaction at low temperatures (preferably at −60 to −100° C.) in an appropriate inert solvent such as tetrahydrofuran or diethylether, preferably under an atmosphere of inert gas, followed by reaction of the lithiated compounds with cyclic carboxylic acid anhydrides of formula IV, or b) by converting compounds of formula III in which R1, R2 and Z have the above-mentioned meanings, in a suitable inert solvent such as, for example, tetrahydrofuran or diethylether into the corresponding Grignard compounds of formula III in which Z represents MgCl, MgBr or MgI followed by reaction of the Grignard compounds with cyclic carboxylic acid anhydrides of formula IV, in which R3 and R4 have the above-mentioned meanings.

Keto acids of formula II, in which R1 and R2 have the same meaning or R2 stands for halogen are preferably prepared by the Friedel-Crafts acylation, while for the preparation of keto acids of formula II, in which R1 and R2 [R2 ≠halogen] have different meanings method a) or b) is preferred.

Compounds of formula III, in which R1 and R2 have the above-mentioned meanings and Z represents a hydrogen (H) or halogen atom, are known or can be prepared by methods known by a person skilled in the art.

Compounds of formula IV, in which R3 and R4 have the above-mentioned meanings are as well known or can be prepared by methods known by a person skilled in the art.

The preparation of hydrazine derivatives of formula R5—NH—NH$_2$ is described, for example, by A. Mertens et al. in J.Med.Chem. 33, 2870–2875, 1990. Further hydrazine derivatives of formula R5—NH—NH$_2$, of which the preparation is explicitly not described, can be prepared in an analogous way or in a way which is known by a person skilled in the art using customary preparation methods.

Method B:

Compounds of formula I in which R1, R2, R3, R4 and R5 have the above-mentioned meanings, X represents —C$_n$H$_{2n}$— or phenylene and Y represents a carboxylate group (—C(O)O—), a carboxamido group (—C(O)NH—) or a sulfonamido group (—SO$_2$—NH—) are preferably prepared by reacting an acid of formula V or an sulfonic acid of formula VI or one of their reactive derivatives (for example an acid halide, an ester or a sulfonyl halide) in which R1, R2, R3 and R4 have the above-mentioned meanings and X represents —C$_n$H$_{2n}$— or phenylene with a phenol of formula R5—OH or an amine of formula R5—NH$_2$, in which R5 has the above-mentioned meanings.

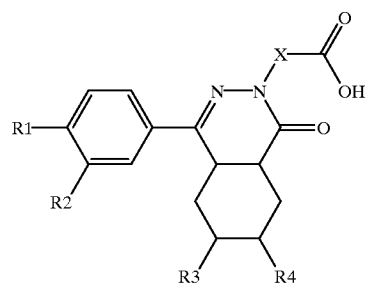

(V)

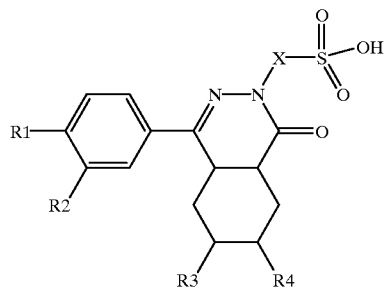

(VI)

The reactions can be performed using customary reaction conditions for example as described in the following examples.

The carboxamide linkage can also be prepared using any coupling method described by M. Bodansky and A. Bodansky in "The Practice of Peptide Synthesis", Springer Verlag, Berlin 1984.

Standard procedures for the preparation of sulfonamides starting from sulfonylchlorides and amines are known to the person skilled in the art.

Acids of formula V or sulfonic acids of formula VI in which X represents phenylene can be prepared analogously to the method described under method A starting from compounds of formula II using a hydrazine derivative such as for example hydrazinobenzoic acid or hydrazinobenzenesulfonic acid.

Acids of formula V or sulfonic acids of formula VI in which X represents —C$_n$H$_{2n}$— can in a first step also be prepared analogously to the method described under method A starting from compounds of formula II using hydrazine hydrate instead of a hydrazine derivative of formula R5—NH—NH$_2$. Deprotonation of the N—H group followed by an alkylation step yields the acids of formula V or the sulfonic acids of formula VI.

The hydrogen atom of the NH—group is removed by a base such as, for example, potassium carbonate, sodium hydroxide, sodium hydride, sodium methanolat or sodium ethanolat in a suitable inert solvent such as dimethylformamide, dimethylsulfoxide, tetrahydrofuran or diethylether. As appropriate alkylation reagents may be mentioned, for example, 4-bromobutanoic acid, ethyl bromacetate or 4-bromobutanesulfonic acid.

Amines of formula R5—NH$_2$ can be prepared, for example, as described by Edgar A. Steck et al., J. Heterocyclic Chem. 1974, 11, 755–761 or as described by B. E. Burpitt in J. Heterocyclic Chemistry, 25, 1689–1695, 1988. Phenols of formula R5—OH can be prepared, for example, as described in EP 0 178 189.

Method C:

Compounds of formula I in which R1, R2, R3, R4 and R5 have the above-mentioned meanings, X represents —C$_n$H$_{2n}$— and Y represents an oxygen or a sulphur atom are preferably prepared by reacting a compound of formula VII

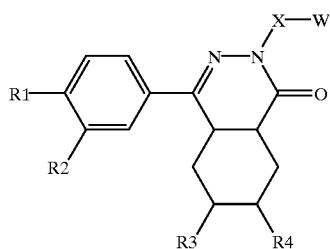

(VII)

In which R1, R2, R3 and R4 have the above-mentioned meanings, X represents —C$_n$H$_{2n}$— and W represents a suitable leaving group, for example a halogen atom, preferably bromine, with a phenol of formula R5—OH or a thiophenol of formula R5—SH, in which R5 has the above-mentioned meanings.

The reaction is preferably carried out under basic conditions in an inert solvent like dimethylformamide, dimethylsulfoxide or tetrahydrofuran.

The compounds of formula VII can be prepared analogously to the method described for the corresponding acids of formula V under method B using in the alkylation step ω,ω'-dihalogenalkanes instead of the ω,ω'-halogenalkanoic acids.

The preparation of phenols of formula R5—OH is described under Method B. Further phenols or thiophenoles of formula R5—OH (R5—SH) can be prepared in an analogous way.

Compounds of formula I in which R1 and/or R2 stand for hydroxyl and R3, R4 and R5 have the above-mentioned meanings are prepared according to one of the methods A, B or C preferably in such a way that the hydroxyl groups are temporarily protected by an appropriate protective group, for example a cyclopentyl group, which can be removed at the end of the reaction sequence.

Suitably, the conversions are carried out analogous to methods which are familiar per se to the person skilled in the art, for example, in the manner which is described in the following examples.

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid or base, or to which the desired acid or base is then added. The salts are obtained by filtering, reprecipitating, precipitating with a non-solvent for the addition salt or by evaporating the solvent. Salts obtained can be converted by basification or by acidifying into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula I, of which the preparation is explicitly not described, can be prepared in an analogous way or in a way which is known by a person skilled in the art using customary preparation methods.

The compounds, which are mentioned in the examples as well as their salts are preferred compounds of the invention.

EXAMPLES

Final products 1. (cis)-4-(3,4-Dimethoxyphenyl)-2-{4-(6-oxo-1,6-dihydro-pyridazin-3-yl)phenyl}-4a,5,8,8a-tetrahydro-2H-phthalazin-1-one 5 mmol of compound A1 (see starting compounds), 5 mmol of compound D1 (see starting compounds) and 5 ml of triethylamine were refluxed for 18 h in 100 ml of 1-propanol. After evaporating the reaction mixture, the residue was dissolved in ethyl acetate and this solution was washed subsequently with 1N hydrochloric acid and aqueous sodium carbonate. After drying over magnesium sulfate the solvent was evaporated. The residue was purified by chromatography (ethyl acetate) and the compound. was crystallized from methanol at −20° C. M.p. 279° C. (decomposition)

2. (cis)-4-(3,4-Dimethoxyphenyl)-2-{4-(4-methyl-6-oxo-1,4,5,6-tetrahydropyridazin-3-yl)phenyl}-4a,5,8,8a-tetrahydro-2H-phthalazin-1-one Prepared from compound A1 and compound D2 (see starting compounds) as described for compound 1. Crystallized from methanol. M.p. 192–194° C.

3. (cis)-4-(3-Cyclopentyloxy-4-methoxyphenyl)-2-{4-(4-methyl-6-oxo-1,4,5,6-tetrahydro-pyridazin-3-yl)phenyl}-4a,5,6,7,8,8a-hexahydro-2H-phthalazin-1-one Prepared from compound A5 (see starting compounds) and compound D2 as described for compound 1. Crystallized from ethyl acetate/petroleum ether (60–80° C.). M.p. 134–141° C.

4. (cis)-N-{4-(4-Methyl-6-oxo-1,4,5,6-tetrahydro-pyridazin-3-yl)phenyl}-4-{4-(3,4-dimethoxyphenyl)-1-oxo-4a,5,8,8a-tetrahydro-1H-phthalazin-2-yl}benzamide Prepared from compound B3 (see starting compounds) and compound C2 as described for compound 9. Crystallized from methanol. M.p. 249–250° C.

5. (cis)-N-{4-(6-Oxo-1,6-dihydro-pyridazin-3-yl)phenyl}-2-[{4-(3,4-dimethoxyphenyl)-1-oxo-4a,5,8,8a-tetrahydro-1H-phthalazin-2-yl}acetamide Prepared from compound B1 (see starting compounds) and compound C1 as described for compound 4. Crystallized from ethyl acetate. M.p. 161–162° C.

6. (cis)-N-{4-(6-Oxo-1,6-dihydro-pyridazin-3-yl)phenyl}-4-[{4-(3,4-dimethoxyphenyl)-1-oxo-4a,5,8,8a-tetrahydro-1H-phthalazin-2-yl}valeramide Prepared from compound B2 (see starting compounds) and compound C1 as described for compound 4. Crystallized from ethyl acetate. Mp: 253° C. (decomposition)

7. (cis)-N-{4-(4-Methyl-6-oxo-1,4,5,6-tetrahydro-pyridazin-3-yl)phenyl}-2-{4-(3,4-dimethoxy-phenyl)-1-oxo-4a,5,8,8a-tetrahydro-1H-phthalazin-2-yl}acetamide Prepared from compound B1 and compound C2 (see starting compounds) as described for compound 4. Crystallized from diethyl ether. M.p. 139–141° C.

8. (cis)-N-{4-(4-Methyl-6-oxo-1,4,5,6-tetrahydro-pyridazin-3-yl)phenyl}-4-{4-(3,4-dimethoxyphenyl)-1-oxo-4a,5,8,8a-tetrahydro-1H-phthalazin-2-yl}valeramide Prepared from compound B2 and compound C2 as described for compound 4. Crystallized from diethyl ether. M.p. 154–157° C.

9. (cis)-N-{4-(6-Oxo-1,6-dihydro-pyridazin-3-yl)phenyl}-4-(4-{3,4-dimethoxyphenyl}-1-oxo-4a,5,8,8a-tetrahydro-1H-phthalazin-2-yl)benzamide A solution of 2.0 g of compound B3 (see starting compounds) and 1.2 g of phosphorus pentachloride in 50 ml of dichloromethane was stirred for 1 h at room temperature and then evaporated. This residue, dissolved in 20 ml of tetrahydrofuran, was added to a solution of 1 g of compound C1 (see starting compounds) and 50 mg of 4-dimethylaminopyridine in 25 ml of pyridine and the resulting solution was left at room temperature for 18 hours. After evaporating the reaction mixture, the residue was dissolved in 100 ml of dichloromethane and this solution was washed subsequently with 1N hydrochloric acid and aqueous sodium carbonate. The organic solution was dried over magnesium sulfate and evaporated. The residue was purified by chromatography (ethyl acetate) and crystallized from methanol. M.p. 272–273° C.

10. (cis)-4-(3,4-Dimethoxy-phenyl)-2-{4-[4(4-(4-methyl-6-oxo-1,4,5,6-tetrahydro-pyridazin-3-yl)-phenoxy]butyl}-4a,5,8,8a-tetrahydro-2H-phthalazin-1-one A mixture of 2.1 g of compound E2 (see starting compounds), 1.0 g of compound E1 (see starting compounds) and 2 g of potassium carbonate in 50 ml of dimethylformamide was heated at 90° C. After 30 minutes, 150 ml of water was added to the reaction mixture and the resulting mixture extracted with diethyl ether. The ether solution was dried over magnesium sulfate and evaporated. The residue was purified by chromatography (ethyl acetate) and the compound crystallized from ethyl acetate. M.p. 94–97° C.

11. (cis)-N-{3-(6-methyl-2-oxo-2H-1,3,4-thiadiazin-5-yl)phenyl}-2-{4-(3,4-dimethoxyphenyl)-1-oxo-4a,5,8,8a-tetrahydro-1H-phthalazin-2-yl}acetamide Prepared from compound B1 and compound F1 as described for compound 9. Purified by chromatography [ethyl acetate: petroleum ether (60–80° C.), 1:1]. M.p. 157–161° C.

12. (cis)-4-(3-chloro-4-methoxyphenyl)-2-{4-(4-methyl-6-oxo-1,4,5,6-tetrahydropyridazin-3-yl)phenyl}-4a,5,8,8a-tetrahydro-2H-phthalazin-1-one A solution of 10 mmol of compound D2, 10 mmol of compound A3 and 1 g of pyridine hydrochloride in 50 ml of pyridine was refluxed for 6 h. After evaporating the solvent, the residue was dissolved in ethyl acetate and this solution was washed successively with 2N hydrochloric acid and aqueous sodium carbonate. After drying over magnesium sulfate, the solvent was evaporated. The compound was crystallized from methanol. M.p. 198–201° C.

13. (cis)-6-(4-[4-{4-(3-Chloro-4-methoxyphenyl)-1-oxo-4a,5,8,8a-tetrahydro-2H-phthalazin-2-yl}-1-butyloxy)phenyl]-4,5-dihydro-5-methyl-2H-pyridazin-3-one Prepared from compound E3 and compound E1 as described for compound 10. M.p. 105–106° C.

14. (cis)-4-(3,4-diethoxyphenyl)-2-{4-(4-methyl-6-oxo-1,4,5,6-tetrahydropyridazin-3-yl)phenyl}-4a,5,8,8a-tetrahydro-2H-phthalazin-1-one Prepared from compound D2 and compound A4 as described for compound 12. Crystallized from diethyl ether. M.p. 164–165° C.

15. (cis)-6-(4-[4-{4-(3,4-diethoxyphenyl)-1-oxo-4a,5,8,8a-tetrahydro-2H-phthalazin-2-yl}-1-butyloxy)phenyl]-4,5-dihydro-5-methyl-2H-pyridazin-3-one Prepared from compound E4 and compound E1 as described for compound 10. Crystallized from methanol. M.p. 73–78° C.

16. (4aS,8aR)-4-[4-{4-(3,4-dimethoxyphenyl)-1-oxo-4a,5,8,8a-tetrahydro-2H-phthalazin-2-yl}phenyl]-5,6-dihydro-5-methylpyridazin-1-one Prepared from compound A2 and compound D2 as described for compound 12. Crystallized from diethyl ether. M.p. 197–199° C.

Starting compounds

A1. (cis)-2-(3,4-Dimethoxybenzoyl)-1,2,3,6-tetrahydrobenzoic acid 0.5 mole of 1,2-dimethoxybenzene was added slowly to a suspension of 0.5 mole aluminiumtrichloride in 1 l of dichloromethane at 0° C. After complete addition, cis-1,2,3,6-tetrahydrophthalic acid anhydride was added to the solution. After 8 hours of reflux the solution was poured onto ice. The organic layer was dried over magnesium sulfate and evaporated. The residue was washed with diethyl ether and dried. M.p. 110–112° C.

A2. (4aS,8aR)-2-(3,4-Dimethoxybenzoyl)-1,2,3,6-tetrahydrobenzoic acid

A mixture of 0.1 mole of compound A1 and 0.1 mole of (1R, 2S)-ephedrine in 800 ml of ethyl acetate was stirred for 15 h after which the precipitate was filtered off. M.p. (ephedrine salt). 135–137° C. Preparation of the free acid: A suspension of the ephedrine salt in ethyl acetate was treated four times with a 0.1 M solution of citric acid after which the ethyl acetate solution was dried over magnesium sulfate and evaporated. The free carboxylic acid was crystallized from diethyl ether. M.p. 127–128° C.

A3. (cis)-2-(3-chloro-4-methoxybenzoyl)-1,2,3,6-tetrahydrobenzoic acid 0.5 mole of 2-chloroanisole was added slowly to a suspension of 0.5 mole aluminiumtrichloride in 1 l of dichloromethane at 0° C. After complete addition, cis-1,2,3,6-tetrahydrophthalic anhydride was added to the solution. After 8 hours of reflux the solution was poured into ice-cold water. The precipitate was filtered off, washed with water and diethyl ether and dried. M.p. 183–185° C.

A4. (cis)-2-(3,4-diethoxybenzoyl)-1,2,3,6-tetrahydrobenzoic acid

Prepared from 1,2-Diethoxybenzene and cis-1,2,3,6-tetrahydrophthalic anhydride as described for compound A3. M.p. 125–127° C.

A5. (cis)-2-(3-Cyclopentyloxy-4-methoxybenzoyl)-cyclohexanecarboxylic acid

4-Bromo-2-cyclopentyloxy-1-methoxybenzene (16.3 g, 60 mmol) was dissolved in THF (200 ml) and cooled with an ethanol/$N_2$ bath to −90° C. BuLi (41 ml, 66 mmol) was added dropwise while keeping the temperature below −80° C. and stirred for another 15 min after the last addition. This mixture was then quickly added under a nitrogen atmosphere to a cooled solution (−90 0° C.) of cis-1,2-cyclohexanedicarboxylic anhydride (11.1 g, 72 mmol) in THF (200 ml). After stirring for 2 h at −80° C. solid ammonium chloride was added and the reaction mixture was allowed to warm slowly to room temperature. Water (300 ml) was added and the anorganic layer was washed with ethyl acetate (200 ml). The combined organic extracts were washed with water (300 ml) and brine (2×300 ml), dried ($MgSO_4$) and the solvent removed under reduced pressure. The residue was dissolved in dichloromethane and purified by chromatography (petroleum ether (60–95° C.)/ethyl acetate: 7/13) and crystallized from petroleum ether (60–95° C.)/ethyl acetate to give the title compound (10.1 g) as a white solid. M.p. 120–121° C.

B1. (cis)-{4-(3,4-Dimethoxyphenyl)-1-oxo-4a,5,8,8a-tetrahydro-2H-phthalazin-2-yl}acetic acid 6 mmol of a 60% suspension of sodium hydride in mineral oil was added to a suspension of 5 mmol of compound B4 in about 40 ml of dimethylformamide, under a flow of nitrogen at room temperature. After stirring this mixture for 30 minutes, 7 mmol of ethyl bromoacetate was added and the resulting mixture was stirred for another 4 hours, after which the solvent was evaporated. The residue was partitioned between ethyl acetate and water, the organic layer was dried over magnesium sulfate and evaporated. The residue was purified by chromatography (dichloromethane). The resulting compound was saponified by stirring for 3 h at room temperature in a mixture of 2N NaOH, THF and methanol (2:1:1). After removal of the organic solvents under reduced pressure, the solution was acidified with hydrochloric acid and extracted with ethyl acetate. The organic solution was dried over magnesium sulfate and evaporated. The compound was crystallized from ethyl acetate. M.p. 178–180° C.

B2. (cis)-5-{4-(3,4-Dimethoxyphenyl)-1-oxo-4a,5,8,8a-tetrahydro-2H-phthalazin-2-yl}acetic acid Prepared from compound B4 and ethyl 5-bromovalerate as described for compound B1. Crystallized from diethyl ether. M.p. 107–108° C.

B3. (cis)-4-{4-(3,4-Dimethoxyphenyl)-1-oxo-4a,5,8,8a-tetrahydro-2H-phthalazin-2-yl}benzoic acid 5 mmol of compound A1, 5 mmol of 4-hydrazinobenzoic acid and 5 ml of triethylamine were refluxed for 18 h in 100 ml of 1-propanol. After evaporating the reaction mixture, the residue was dissolved in ethyl acetate. Purified by chromatography (ethyl acetate) and crystallized from ethyl acetate. M.p. 198–199° C.

B4. (cis)-4-(3,4-Dimethoxyphenyl)-4a,5,8,8a4etrahydro-2H-phthalazin-1-one

A solution of 26 g of compound A1 and 19 g of hydrazine hydrate was refluxed for 4 h in ethanol. After cooling to room temperature, the precipitate was filtered off and dried. M.p. 173–174° C.

B5. (cis)-4-(3-Chloro-4-methoxyphenyl)-4a,5,8,8a-tetrahydro-2H-phthalazin-1-one

Prepared from compound A3 and hydrazine hydrate as described for compound B4. M.p. 183–185° C.

B6. (cis)-4-(3,4-Diethoxyphenyl )-4a,5,8,8a-tetrahydro-2H-phthalazin-1-one

Prepared from compound A4 and hydrazine hydrate as described for compound B5. M.p. 145–147° C.

C1. 6-(4-Aminophenyl)-2H-pyridazin-3-one

Prepared as described by E. A. Steck et al., J. Heterocyclic Chem. 1974, 11, 755–761.

C2. 6–4-Aminophenyl)-5-methyl4,5-dihydro-2H-pyridazin-3-one

Prepared as described by B. E. Burpitt, L. P. Crawford, B. J. Davies, J. Mistry, M. B. Mitchell and K. D. Pancholi in J. Heterocyclic Chemistry, 25,1689–1695 (1988).

D1. 6-(4-Hydrazinophenyl)-2H-pyridazin-3-one

Prepared from compound C1 analogous to the method described for D2.

D2. 6-(4-Hydrazinophenyl)-5-methyl-4,5-dihydro-2H-pyridazin-3-one

Prepared from compound C2 as described by A. Mertens et al., J. Med. Chem. 1990, 33, 2870–2875.

E1. 6-(4-Hydroxyphenyl)-4,5-dihydro-5-methyl-2H-pyridazin-3-one

Prepared as described by Y. Morisawa et al. (Sankyo Co) EP178189.

E2. (cis)-2-(4-Bromo-1-butyl)-4-(3,4-dimethoxyphenyl)-4a,5,8,8a-tetrahydro-2H-phthalazin-1-one 25 g of 1,4-dibromobutane was added to a mixture of 10 g of compound B4, 4 g of a 60% suspension of sodium hydride in mineral oil in 150 ml of dimethylformamide. The resulting mixture was stirred for 18 hours at room temperature. 300 ml of water was added and the resulting mixture extracted with diethyl ether. The organic solution was dried over magnesium sulfate and evaporated. The residue was purified by chromatography [ethyl acetate: petroleum ether (60–80° C.)/1:4] and the compound crystallized from petroleum ether (60–80° C.). M.p. 102–103° C.

E3. (cis)-2-(4-Bromobutyl)-4-(3-chloro4-methoxyphenyl)-4a,5,8,8a-tetrahydro-2H-phthalazin-1-one Prepared from 1,4-dibromobutane and compound B5 as described for compound E2. Oil 1H-NMR(CDCl$_3$): 1.75–2.31 (m,7H,3xcyclohexene-H, 2×CH$_2$); 2.72–2.84 (m,1H,cyclohexe-H); 2.88–3.08 (m,1H, cyclohexene-H); 3.22–3.40(m,1H, cyclohexene-H); 3.39–3.54 (m,2H,N—CH$_2$); 3.71–4.10 (m,5H,O—CH$_3$, Br—CH$_2$); 5.57–5.87 (m,2H,CH=CH); 6.96 (d,J=8.6Hz, 1H,Ar—H); 7.59–7.71 (m,1H, Ar—H); 7.82 (s,1H,Ar—H).

E4. (cis)-2-(4-Bromobutyl)-4-(3,4-diethoxyphenyl)-4a,5,8,8a-tetrahydro-2H-phthalazin-1-one Prepared from 1,4-dibromobutane and compound B6 as described for compound E2. M.p. 73–75° C.

F1. 5-(3-amino phenyl)-6-methyl-3,6-dihydro-1,3,4-thiadiazin-2-one

A solution of 1.5 ml of 2N hydrochloric acid was added slowly to a stirred mixture of 10 mmol of compound F2, 4 g of iron powder, 20 ml of water and 70 ml of ethanol at 70° C. After complete addition, the mixture was stirred for another 30 minutes. After filtering, the reaction mixture was concentrated under reduced pressure and the residue extracted with dichloromethane. This dichloromethane solution was dried over magnesium sulfate and evaporated. The residue was washed with diethyl ether and dried. M.p. 167–170° C.

F2. 5-(3-nitrophenyl)-6-methyl-3,6-dihydro-1,3,4-thiadiazin-2-one

A solution of 25 mmol of compound F3, 30 mmol of O-methyl thiocarbazate (K. Rüfenacht, Helv. Chim. Acta 1968, 51, 518–522) and 5 ml of 2-propanol, saturated with hydrochloric acid, in 100 ml of absolute ethanol was refluxed for 1 hour. After evaporating the solution, the residue was dissolved in dichloromethane and this solution was washed with aqueous sodium carbonate. The dichloromethane solution was dried over magnesium sulfate and evaporated. The residue was purified by chromatography [ethyl acetate: petroleum ether (60–80° C.), 1:4]. The compound was crystallized from a mixture of diethyl ether and petroleum ether (60–80° C.). M.p. 169–172° C.

F3. 3'-nitro-2-bromoproplophenone 50 mmol of bromine was added to a stirred solution of 50 mmol of 3'-nitropropiophenone in 250 ml of acetic acid at room temperature. After complete addition, the solution was stirred for another 10 minutes and subsequently evaporated. The residue was dissolved in ethyl acetate (about 250 ml) and this solution was washed with aqueous sodium carbonate. After drying over magnesium sulfate, the solvent was evaporated. The residue was washed with diethyl ether (about 50 ml) and dried. M.p. 61–64° C.

Commercial Utility

The compounds according to the invention have valuable pharmacological properties which make them commercially utilizable. As selective inhibitors of type 3 and 4 of cyclic nucleotide phosphodiesterase (PDE3, PDE4), they are suitable on the one hand as bronchial therapeutics (for the treatment of airway obstructions on account of their dilating and cilium-stimulating action but also on account of their respiratory rate- and respiratory drive-increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumor necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin), neurogenic mediators (such as substance P, neurokinin), proteins such as, for example, granular contents of leukocytes (inter alia cationic proteins of eosinophils) and adherent proteins (e.g. integrins). The compounds according to the invention have smooth muscle-relaxant action, e.g. in the region of the bronchial system, of the blood circulation, and of the efferent urinary passages. Furthermore they have a cilium-frequency increasing action, e.g. in the bronchial system.

In this context, the compounds according to the invention are distinguished by low toxicity, good human acceptance, good enteral absorption and high bioavailability, great therapeutic breadth, the absence of significant side effects and good water solubility.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origin (bronchitis, allergic bronchitis, bronchial asthma, COPD); disorders with a reduction of the cilium activity or with increased demands on the ciliar clearance (bronchitis, mucoviscidose); dermatoses (especially of proliferative, inflammatory and allergic type) such as, for example, psoriasis (vulgaris), toxic and allergic contact eczema, atopic eczema, seborrheic eczema, lichen simplex, sunburn, pruritis in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (Type I, autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; and also disorders of the central nervous system such as memory disorders and Alzheimer's disease, candidiasis, leishmaniases and leprosy.

On account of their vasorelaxant activity, the compounds according to the invention can also be used for the treatment of high blood pressure disorders of various origin such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as antithrombotic, platelet aggregation-inhibiting substances.

The invention further relates to a method for the treatment of mammals including humans who are suffering from one of the above-mentioned diseases. The method comprises administering a therapeutically effective and pharmacologically tolerable amount of one or more of the compounds according to the invention to the sick mammal.

The invention further relates to the compounds according to the invention for use in the treatment and/or prophylaxis of diseases, especially the diseases mentioned.

The invention also relates to the use of lthe compounds according to the invention for the production of medicaments which are employed for the treatment and/or prophylaxis of the diseases mentioned.

The invention furthermore relates to medicaments for the treatment and/or prophylaxis of the diseases mentioned and which contain one or more of the compounds according to the invention.

Advantageously, the substances according to the invention are also suitable for combination with other substances which bring about stimulation of cAMP, such as prostaglandins (PGE2, PGI2 and prostacyclin) and their derivatives, direct adenylate cyclase stimulators such as forskolin and related substances, or substances indirectly stimulating adenylate cyclase, such as catecholamines and adrenergic receptor agonists, in particular beta mimetics. In combination, on account of their CAMP degradation-inhibiting action, they in this case display a synergistic, superadditive activity. This comes to bear, for example, in their use in combination with PGE2 for the treatment of pulmonary hypertension.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterases of type 3 and 4 (PDE3/4), ameliorating the symptoms of an PDE3/4-mediated disorder, and wherein the packaging material comprises a label or package insert which indicates that the pharmaceutical agent is useful for preventing or treating PDE3/4-mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The medicaments are prepared by methods known per se familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, ointments bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are administered either directly as a powder (preferably in micronized form) or by atomization of solutions or suspensions which contain them. With respect to the preparations and administration forms, reference is made, for example, to the details in European Patent 163 965.

For the treatment of dermatoses, the compounds according to the invention are used in particular in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be nmentioned are, for example, powders, emulsions, suspensions, sprays, oils, ointments, fatty ointments, creams, pastes, gels or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.01 and 10 mg/kg per day.

Biological Investigations

In the investigation of PDE4 inhibition at the cellular level, the activation of inflammatory cells has particular importance. An example which may be mentioned is the FMLP (N-formylmethionylleucylphenylalanine)-induced superoxide production of neutrophilic granulocytes, which can be measured as luminol-potentiated chemiluminescence [McPhail L C, Strum S L, Leone P A and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit chemiluminescence, and/or cytokine secretion, and/or the secretion of inflammation-increasing mediators in inflammatory cells, like T-lymphocytes, monocytes, macrophages and granulocytes are those which inhibit PDE4 or PDE3 and PDE4. The latter isoenzyme of the phosphodiesterase families is particularly represented in granulocytes. Its inhibition leads to an increase in the intracellular cyclic AMP concentration and thus to the inhibition of cellular activation. PDE4 inhibition by the substances according to the invention is thus a central indicator of the suppression of inflammatory processes. (Giembycz MA, Could isoenzyme-selective phosphodiesterase inhibitors render bronchodilatory therapy redundant in the treatment of bronchial asthma? Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE3/4 inhibitor. In "New Drugs for Asthma Therapy", 379–402, Birkhaüser Verlag Basel 1991; Schudt C et al., Influence of selective phosphodiesterase inhibitors on human neutrophil functions and levels of cAMP and Ca. Naunyn-Schmiedebergs Arch Pharmacol 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE3/4-inhibitors. In "Phosphodiesterase Inhibitors", 147–160, "The Handbook of Immunopharmacology", Academic Press, 1996.

A. Methodology

1. Inhibition of PDE isoenzymes

The PDE activity was determined according to Thompson et al. (1) with some modifications (2). The test samples contained 40 mM tris HCl (pH 7.4), 5 mM $MgCl_2$, 0.5 $\mu M$ cAMP or cGMP, [$^3$H] cAMP or [$^3$H]cGMP (about 50,000 cpm/sample), the PDE isoenzyme-specific additions described in greater detail below, the indicated concentrations of inhibitor and an aliquot of the enzyme solution in a total sample volume of 200 $\mu l$. Stock solutions of the compounds to be investigated in DMSO were prepared in concentrations such that the DMSO content in the test samples did not exceed 1% by volume—to avoid an effect on the PDE activity. After preincubation at 37° C. for 5 minutes, the reaction was started by addition of the substrate (cAMP or cGMP). The samples were incubated at 37° C. for a further 15 min. The reaction was terminated by addition of 50 $\mu l$ of 0.2N HCl. After cooling on ice for 10 minutes and addition of 25 $\mu g$ of 5'-nucleotidase (snake venom from Crotalus atrox), the mixture was again incubated at 37° C. for 10 min and the samples were then applied to QAE Sephadex A-25 columns. The columns were eluted with 2 ml of 30 mM ammonium formate (pH 6.0). The radioactivity of the eluate was measured and corrected by the corresponding blank values. The proportion of hydrolyzed nucleotide in no case exceeded 20% of the original substrate concentration.

PDE1 ($Ca^{2+}$/calmodulin-dependent) from bovine brain: the inhibition of this isoenzyme was investigated in the presence of $Ca^{2+}$ (1 mM) and calmodulin (100 nM) using cGMP as a substrate (3).

PDE2 (cGMP-stimulated) from rat hearts was purified chromatographically [Schudt et al. (4)] and investigated in the presence of cGMP (5 $\mu M$) using cAMP as a substrate.

PDE3 (cGMP-inhibited) and PDE5 (cGMP-specific) were investigated in homogenates of human blood platelets [Schudt et al. (4)] using cAMP or cGMP as a substrate.

PDE4 (cAMP-specific) was investigated in the cytosol of human polymorphonuclear leukocytes (PMNL) [isolated from leukocyte concentrates, see Schudt et al. (5)] using cAMP as a substrate. The PDE3 inhibitor motapizone (1 $\mu M$) was used in order to suppress the PDE3 activity emanating from contaminating blood platelets.

2. Statistics

The $IC_{50}$ values were determined from the concentration-inhibition curves by nonlinear regression using the Graph-Pad InPlot™ program (GraphPad Software Inc., Philadelphia, USA).

3. References (1) Thompson W. J., Terasaki W. L., Epstein P. M. and Strada S. J., Assay of cyclic nucleotide phosphodiesterase and resolution of multiple molecular forms of the enzyme; Adv. Cycl. Nucl. Res. 1979, 10, 69–92

(2) Bauer A. C. and Schwabe U., An improved assay of cyclic 3',5'-nucleotide phosphodiesterase with QAE Sephadex A-25; Naunyn-Schmiedeberg's Arch. Pharmacol. 1980, 311, 193–198

(3) Gietzen K., Sadorf I. and Bader H., A model for the regulation of the calmodulin-dependent enzymes erythrocyte $Ca^{2+}$-transport ATPase and brain phosphodiesterase by activators and inhibitors; Biochem. J. 1982, 207, 541–548.

(4) Schudt C., Winder S., Müller B. and Ukena D., Zardaverine as a selective inhibitor of phosphodiesterase isoenzymes; Biochem. Pharmacol. 1991, 42, 153–162

(5) Schudt C., Winder S., Forderkunz S., Hatzelmann A. and Ullrich V., Influence of selective phosphodiesterase inhibitors on human neutrophil functions and levels of cAMP and Ca; Naunyn-Schmiedeberg's Arch. Pharmacol. 1991, 344, 682–690

B. Results

In Table 2 below, the inhibitory concentrations determined according to Section A1 [inhibitory concentrations as -log $IC_{50}$ (mol/l)] for the compounds according to the invention are indicated for the PDE3 and PDE4 isoenzymes. The numbers of the compounds correspond to the numbers of the examples.

TABLE 2

| Compound | [-log $IC_{50}$ mol/l] | |
|---|---|---|
| | PDE4 | PDE3 |
| 2 | 8.36 | 6.69 |
| 4 | 8.48 | 6.05 |
| 5 | 8.10 | 5.90 |
| 6 | 8.17 | 6.08 |
| 7 | 8.40 | 6.74 |
| 8 | 8.17 | 7.00 |
| 9 | 9.08 | 5.31 |
| 12 | 7.00 | 7.09 |
| 13 | 7.77 | 7.45 |
| 14 | 8.05 | 6.56 |
| 15 | 8.60 | 6.68 |
| 16 | 8.64 | 6.36 |

What is claimed is:

1. A compound of formula I

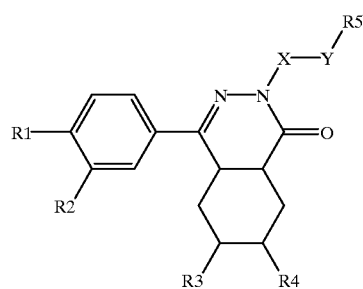

(I)

in which
R1 is hydroxyl, 1–4C-alkoxy, or 1–4C-alkoxy which is completely or predominantly substituted by fluorine,
R2 is hydroxyl, halogen, 1–8C-alkoxy, 3–7C-cycloalkoxy, 3–7C-cycloalkylmethoxy, or 1–4C-alkoxy which is completely or predominantly substituted by fluorine,
R3 and R4 are both hydrogen or together form an additional bond,
and in which either
X is a covalent bond and
Y is a covalent bond,
or
X is —$C_nH_{2n}$— and
Y is O (oxygen), S (sulfur), carboxylate (—C(O)—O—), carboxamido (—C(O)NH—) or sulfonamido (—S(O)$_2$—NH—),
or
X is phenylene and
Y is carboxylate (—C(O)O—), carboxamido (—C(O)NH—) or sulfonamido (—S(O)$_2$NH—), R5 represents a radical of formula (a)

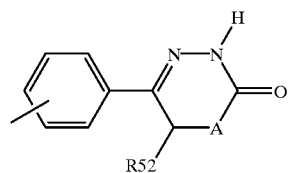

(a)

wherein
A is S (sulphur) or —CH(R51)—,
R51 is hydrogen or 1–4C-alkyl,
R52 is hydrogen or 1–4C-alkyl, or wherein
R51 and R52 together form an additional bond,
n is an integer from 1 to 4, or a salt of thereof.

2. A compound of formula I according to claim 1 in which
R1 is hydroxyl, 1–4C-alkoxy, or 1–2C-alkoxy which is completely or predominantly substituted by fluorine,
R2 is hydroxyl, halogen, 1–4C-alkoxy, 3–5C-cycloalkoxy, 3–5C-cycloalkylmethoxy, or 1–2C-alkoxy which is completely or predominantly substituted by fluorine,
R3 and R4 are both hydrogen or together form an additional bond,
and in which either
X is a covalent bond and
Y is a covalent bond
or
X is —$C_nH_{2n}$— and
Y is O (oxygen), carboxamido (—C(O)NH—) or sulfonamido (—S(O)$_2$NH—),
or
X is phenylene and
Y is carboxamido (—C(O)NH—) or sulfonamido (—S(O)$_2$NH—),
R5 represents a radical of the formula (a)

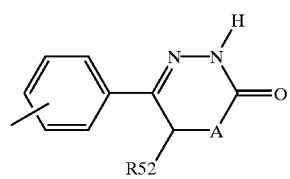

(a)

wherein
A is S (sulphur) or —CH(R51)—,
R51 is hydrogen or 1–2C-alkyl,
R52 is hydrogen or 1–2C-alkyl, or wherein
R51 and R52 together form an additional bond,
n is an integer from 1 to 4, or a salt of thereof.

3. A compound of formula I according to claim 1 in which
R1 is methoxy, ethoxy or difluoromethoxy,
R2 is chlorine, methoxy, ethoxy, difluoromethoxy or cyclopentyloxy,
R3 and R4 are both hydrogen or together form an additional bond,
and in which either
X is a covalent bond and
Y is a covalent bond or
X is —$C_nH_{2n}$— and
Y is O (oxygen) or carboxamido (—C(O)NH—)
or
X is phenylene and
Y is carboxamido (—C(O)NH—),
R5 represents a radical of formula (a)

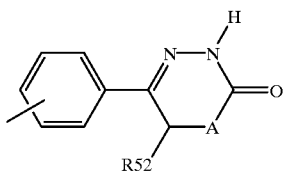

(a)

wherein
A is S (sulphur) or —CH(R51)—,
R51 is hydrogen,
R52 is methyl, or wherein
R51 and R52 together form an additional bond,
n is an integer from 1 to 4, or a salt of thereof.

4. A compound of formula I according to claim 1 in which
R1 is methoxy or ethoxy,
R2 is chlorine, methoxy, ethoxy or cyclopentyloxy,
R3 and R4 are both hydrogen or together form an additional bond, and in which either
X is a covalent bond and
Y is a covalent bond
or
X is —$C_nH_{2n}$— and
Y is O (oxygen) or carboxamido (—C(O)NH—)
or
X is phenylene and
Y is carboxamido (—C(O)NH—),
R5 represents a radical of formula (a)

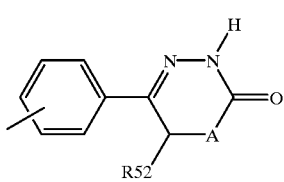

(a)

wherein
A is S (sulphur) or —CH(R51)—,
R51 is hydrogen,
R52 is methyl, or wherein
R51 and R52 together form an additional bond,
n is an integer from 1 to 4, or a salt of thereof.

5. A compounds of formula I according to claim 1 in which
R1 is methoxy,
R2 is methoxy or cyclopentyloxy,
R3 and R4 are both hydrogen or together form an additional bond,
and in which either
X is a covalent bond and
Y is a covalent bond
or
X is —$C_nH_{2n}$— and
Y is O (oxygen) or carboxamido (—C(O)NH—)
or
X is phenylene and
Y is carboxamido (—C(O)NH—),
R5 represents a radical of formula (a)

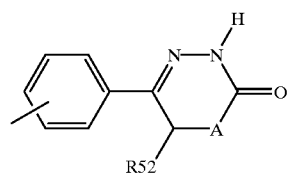

(a)

wherein
A is S (sulphur) or —CH(R51)—,
R51 is hydrogen,
R52 is methyl, or wherein
R51 and R52 together form an additional bond,
n is an integer from 1 to 4, or a salt of thereof.

6. A pharmaceutical composition comprising an effective amount of a compound according to claim 1 or a pharmaceutically acceptable salt thereof together with a customary pharmaceutical or auxiliary and/or carrier.

7. A method of treating an airway disorder which comprises administering an effective amount of a compound according to claim 1 or a pharmaceutically acceptable salt thereof to a subject afflicted with such disorder.

8. A method of compounding a medicament composition by combining a usual pharmaceutical auxiliary and/or carrier with a pharmaceutically acceptable compound for treating an airway disorder, and wherein the compound is a compound according to claim 1 or a pharmaceutically acceptable salt thereof.

* * * * *